United States Patent [19] [11] 4,148,793
Danziger et al. [45] Apr. 10, 1979

[54] PROCESS FOR THE PURIFICATION OF EPSILON-CAPROLACTAM

[75] Inventors: Harry Danziger, Krefeld; Ludwig Deibele, Cologne; Bernd-Ulrich Kaiser, Krefeld, all of Fed. Rep. of Germany

[73] Assignee: Bayer Aktiengesellschaft, Leverkusen, Fed. Rep. of Germany

[21] Appl. No.: 832,002

[22] Filed: Sep. 9, 1977

[30] Foreign Application Priority Data

Sep. 15, 1976 [DE] Fed. Rep. of Germany ....... 2641454

[51] Int. Cl.$^2$ ............................................ C07D 201/16
[52] U.S. Cl. ............................................... 260/239.3 A
[58] Field of Search ................................. 260/239.3 A

[56] References Cited

U.S. PATENT DOCUMENTS

| | | | |
|---|---|---|---|
| 2,221,369 | 11/1940 | Cass | 260/239.3 A |
| 3,755,305 | 8/1973 | Schwarz et al. | 260/239.3 A |
| 3,792,045 | 2/1974 | Henn et al. | 260/239.3 A |
| 3,794,647 | 2/1974 | Henn et al. | 260/239.3 A |
| 3,882,102 | 5/1975 | Immel et al. | 260/239.3 A |
| 3,944,543 | 3/1976 | Goettsch et al. | 260/239.3 A |

Primary Examiner—Natalie Trousof
Assistant Examiner—Robert T. Bond
Attorney, Agent, or Firm—Connolly and Hutz

[57] ABSTRACT

Process for the removal of residues of solvent from crystallized ε-caprolactam, wherein the major quantity of solvent is removed in a first stage by distillation in the presence of water in an amount so that the water content of the residue of the first stage is from 0.5 to 6% by weight, and in a second stage by distilling water and any residues of solvent still present.

1 Claim, No Drawings

PROCESS FOR THE PURIFICATION OF EPSILON-CAPROLACTAM

It is known that crude caprolactam can be purified by crystallisation from toluene. This can be done with ε-caprolactam from various scources, for example, from the Beckmann rearrangement of cyclohexanone oxime with oleum, from the rearrangement of cyclohexanone oxime in the gas phase in the presence of boric acid catalysts, from the decomposition of polyamides or from other manufacturing processes. After crystallisation from toluene, the caprolactam may be further purified by distillation if an exceptionally high degree of purity is required.

The distillation of ε-caprolactam is very difficult and in most cases requires a high vacuum and additives such as sodium hydroxide. The addition of sodium hydroxide results in residues which are not further processable and which constitute a loss of material. There is therefore an urgent interest to avoid distillation in the purification of caprolactam.

If ε-caprolactam is crystallised from a solvent and an attempt is made to distill the solvent residues (such as toluene) from the caprolactam, a low quality product is obtained. For example, it turns cloudy when mixed with water, and even the addition of water during distillation of the organic solvent hardly provides any improvement.

Attempts to remove residues of the organic solvent by drying the caprolactam crystals in a stream of nitrogen or air (20°–60° C., 10–760 mm Hg-pressure) have been equally unsuccessful. The caprolactam obtained in this way had an unpleasant smell.

This invention provides a process for the removal of residues of organic solvent from crystallized ε-caprolactam in two stages. In the first stage, the major quantity of solvent is removed by distillation in the presence of water which is added or already contained in the caprolactam in an amount so that the residue obtained from the first stage contains from 0.5 to 6% by weight of water, and in the second stage the water and residues of solvents still left are then removed by distillation.

By this method, the distillation of ε-caprolactam is avoided. The caprolactam finally obtained has excellent characteristics. The process is applicable to ε-caprolactam from any source provided it contains an organic solvent in quantities of, preferably, from 0.1 to 10% by weight. The solvents used are normally benzene, xylenes or ethylbenzene, but toluene is preferred.

The quantities of water added are approximately 0.5 to 3 parts by weight, based on the weight of organic solvent. In the first stage, the process is preferably operated so that the concentration of solvent in the sump obtained from the first stage is less than 0.1%.

The first stage of the process, generally, requires a pressure of from 100 to 760 Torr and the second stage a pressure of from 10 to about 100 Torr.

In the following Examples the percentages are by weight.

EXAMPLE 1

4 parts by weight of water were added to 100 parts by weight of a mixture of 98% of lactam and 2% of toluene obtained by purifying a crude caprolactam by extracting it with toluene and crystallising it twice from toluene. This crude caprolactam had been obtained by gas phase rearrangement of cyclohexanone oxime in the presence of catalysts containing boric acid. After the aforesaid addition of 4 parts by weight of water to the mixture of lactam and toluene, the mixture was passed through a continuously operating horizontal evaporator (first stage).

At a pressure of 300 Torr and a sump temperature of 135° C., the sump product of the evaporator contained 1.8% of water and traces of toluene (less than 100 ppm).

The sump product was transferred to a second horizontal evaporator (second stage) which was operated at 12 Torr and a sump temperature of 150° C.

The sump product obtained was a pure lactam which had the following characteristics:
m.p.: 69.10° C.,
UV-index: 95

EXAMPLE 2

100 parts by weight of a mixture of 90% of lactam and 10% of toluene, obtained by carrying out a Beckmann rearrangement of cyclohexanone oxime in oleum followed by neutralisation with $NH_3$, extraction with toluene and preliminary concentration, were dried in two stages under the conditions indicated in Example 1 after the addition of 10 parts by weight of water.

The sump product of the first stage contained 1.6% of water.

The dried product was distilled in a high vacuum with the addition of 2% of NaOH.
Characteristics:
m.p.: 69.10° C.
UV index: 94

EXAMPLE 3

100 parts by weight of a lactam mixture analogous to that of Example 2, but containing benzene instead of toluene, were dehydrated as in Example 1 after the addition of 6 parts by weight of water, but with the difference that, in the first stage, the pressure was 360 Torr and the sump temperature was 130° C.

The water content of the first stage was 2.0%.

The dehydrated product was distilled as in Example 2.
Characteristics:
m.p.: 69.10° C.
UV index: 95

EXAMPLE 4

100 parts by weight of a mixture of 98% of lactam and 2% of toluene, obtained from the crude lactam resulting from the Beckmann rearrangement of cyclohexanone oxime in oleum followed by neutralisation with $NH_3$, extraction with toluene and crystallisation from toluene, were dehydrated in a manner analogous to Example 1.
Characteristics:
m.p.: 69.10° C.
UV index: 98

We claim:

1. A process for removing solvent present in ε-caprolactam in an amount of 0.1 to 10% by weight which comprises removing solvent from said solvent containing ε-caprolactam in a first stage distillation at a pressure of from 100 to 760 Torr in the presence of about 0.5 to 3 parts by weight of water per part by weight of solvent initially present in said ε-caprolactam until the resulting undistilled ε-caprolactam in the sump has a solvent content of less than 0.1% by weight and a water content of 0.5 to 6% by weight and then subjecting the undistilled ε-caprolactam mixture of said first stage to a second stage water and solvent distillation at a pressure of from 10 to about 100 Torr whereby additional water and solvent are removed, and recovering from the distillation sump pure undistilled ε-caprolactam.

* * * * *